United States Patent
Gallo et al.

(10) Patent No.: US 9,664,649 B2
(45) Date of Patent: May 30, 2017

(54) STRUCTURAL HEALTH MONITORING SYSTEM EMPLOYING ELECTROMECHANICAL IMPEDANCE TECHNOLOGY

(71) Applicants: Embraer S.A., Sao Jose dos Campos—SP (BR); Universidade Federal de Uberlândia, Uberlândia—MG (BR)

(72) Inventors: Carlos Alberto Gallo, Uberlândia (BR); Domingos Alves Rade, Uberlândia (BR); Elias Bitencourt Teodoro, Uberlândia (BR); Luiz Gustavo Martins, Uberlândia (BR); Marcos Morais de Souza, Uberlândia (BR); Roberto Mendes Finzi Neto, Uberlândia (BR); Valder Steffen, Jr., Uberlândia (BR); Camila Gianini Gonsalez, Sao Jose dos Campos (BR); Glauco Humberto Gomes, Sao Jose dos Campos (BR); Fernando Dotta, Sao Jose dos Campos (BR); Mauricio Hartmann, Sao Jose dos Campos (BR); Paulo Anchieta da Silva, Sao Jose dos Campos (BR); Ricardo Pinheiro Rulli, Sao Jose dos Campos (BR)

(73) Assignees: Embraer S.A., São José dos Campos (BR); Universidade Federal de Uberlândia, Uberlândia (BR)

(*) Notice: Subject to any disclaimer, the term of this patent is extended or adjusted under 35 U.S.C. 154(b) by 558 days.

(21) Appl. No.: 14/107,576

(22) Filed: Dec. 16, 2013

(65) Prior Publication Data
US 2015/0168353 A1   Jun. 18, 2015

(51) Int. Cl.
*G01B 5/28* (2006.01)
*G01B 5/30* (2006.01)
(Continued)

(52) U.S. Cl.
CPC .......... *G01N 29/09* (2013.01); *G01M 17/007* (2013.01); *G01N 29/32* (2013.01); *G01N 29/44* (2013.01);
(Continued)

(58) Field of Classification Search
None
See application file for complete search history.

(56) References Cited

U.S. PATENT DOCUMENTS 6,006,163 A   12/1999   Lichtenwalner et al.
7,024,315 B2   4/2006   Giurgiutiu
(Continued)

*Primary Examiner* — David Gray
*Assistant Examiner* — Geoffrey T Evans
(74) *Attorney, Agent, or Firm* — Nixon & Vanderhye P.C.

(57) ABSTRACT

A method to acquire the structural health state of an aircraft mechanical component performs measurements at each frequency point of interest by using a network of transducers and working each one simultaneously as actuator and sensor. Each transducer is individually excited by a sinusoidal, constant frequency and arbitrary amplitude, voltage waveform for each arbitrary frequency point used to interrogate the structure. A dedicated hardware executes an analogical (analog) quantization to measure electrical current and average electrical power consumed by each transducer. With these two variables, the electromechanical signature of the structure is obtained at different areas of the monitored structure.

20 Claims, 5 Drawing Sheets

(51) Int. Cl.
*G01N 29/09* (2006.01)
*G01M 17/007* (2006.01)
*G01N 29/44* (2006.01)
*G01N 29/32* (2006.01)

(52) U.S. Cl.
CPC ... *G01N 29/4472* (2013.01); *G01N 2291/018* (2013.01); *G01N 2291/023* (2013.01); *G01N 2291/0258* (2013.01); *G01N 2291/0289* (2013.01); *G01N 2291/106* (2013.01); *G01N 2291/2694* (2013.01)

(56) References Cited

U.S. PATENT DOCUMENTS

| | | | |
|---|---|---|---|
| 7,487,059 B2 | 2/2009 | Davis et al. | |
| 2003/0009300 A1* | 1/2003 | Giurgiutiu | G01N 29/11 702/35 |
| 2008/0255781 A1 | 10/2008 | Beard et al. | |
| 2008/0319692 A1 | 12/2008 | Davis et al. | |
| 2009/0281736 A1* | 11/2009 | Kim | G01M 5/0041 702/34 |
| 2010/0161283 A1* | 6/2010 | Qing | G01N 29/2475 702/188 |
| 2010/0319452 A1 | 12/2010 | Masuda | |
| 2010/0319455 A1* | 12/2010 | Ihn | G01N 29/069 73/603 |
| 2011/0035167 A1* | 2/2011 | Qing | G01M 5/00 702/58 |
| 2011/0279233 A1* | 11/2011 | Zhang | G01N 29/42 340/10.1 |
| 2012/0068827 A1* | 3/2012 | Yi | G01D 5/18 340/10.1 |

\* cited by examiner

STRUCTURAL HEALTH MONITORING SYSTEM EMPLOYING ELECTROMECHANICAL IMPEDANCE TECHNOLOGY

CROSS-REFERENCE TO RELATED APPLICATIONS

None.

STATEMENT REGARDING FEDERALLY SPONSORED RESEARCH OR DEVELOPMENT

None.

FIELD

The technology herein relates to electronic sensing and analysis, and more particularly to methods, systems and techniques for acquiring the structural health state of an aircraft mechanical component based on ascertaining the mechanical impedance of the component.

BACKGROUND

Aircraft parts can become stressed with use. While techniques are known for automatically analyzing changes in vibrational response, it would be helpful to be able to automatically sense and analyze changes in mechanical impedance using techniques that are less complicated, more efficient and less time consuming.

BRIEF DESCRIPTION OF THE DRAWINGS

These and other features and advantages will be better and more completely understood by referring to the following detailed description of example non-limiting illustrative embodiments in conjunction with the drawings of which.

DETAILED DESCRIPTION

Figure 1:
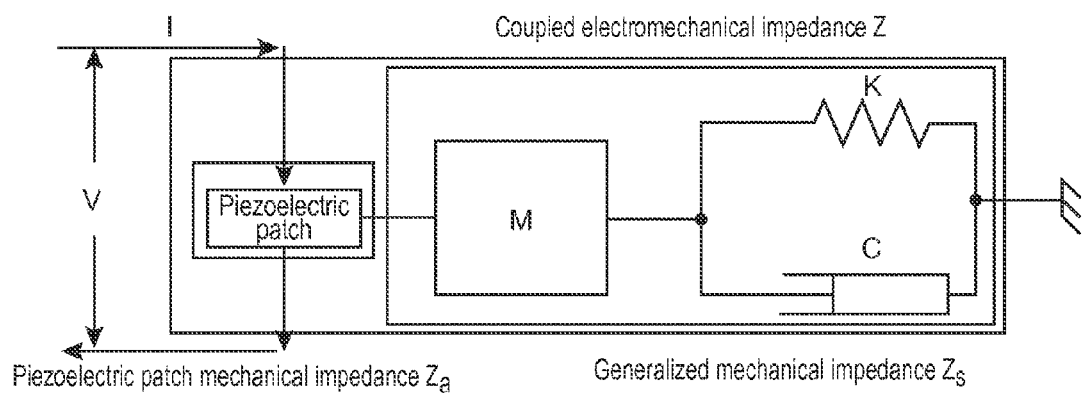
FIG. 1 shows a one-dimensional model of an example electromechanical impedance due to the interaction of a piezoelectric patch and a monitored structure.

FIG. 1 shows the well-known one-dimensional model representation of a mechanical system containing an integrated sensor-actuator piezoelectric patch. The solution of the wave equation for the PZT patch bonded to the structure leads to frequency-dependent electrical admittance given by Equation 1:

$$Y(\omega) = i\omega a\left[\varepsilon_{33}^{-T}(1-i\delta) - \frac{Z_S(\omega)}{Z_S(\omega)+Z_a(\omega)}d_{31}^2 \hat{Y}_{11}^2\right] \quad (1)$$

From Equation 1, $Y(\omega)$ is the electrical admittance (inverse of electrical impedance), $Z_a$ and $Z_s$ are the PZT's and the structure's mechanical impedances, respectively, $\hat{Y}_{11}^2$ is the complex Young's modulus of the PZT in the direction 1 under zero electric field, $d_{31}$ is the piezoelectric coupling constant at zero stress, $\varepsilon_{33}^{-T}$ is the dielectric constant at zero stress, $\delta$ is the dielectric loss tangent of the piezoelectric patch, and a is a geometric constant of the PZT patch.

This equation indicates that the electrical impedance of the PZT wafer bonded onto the structure is directly related to the mechanical impedance of the host structure. The EMI over a range of frequencies is analogous to a frequency response function (FRF) of the structure, which contains vital information regarding structural integrity.

Damage causes direct changes in the structural stiffness and/or damping and alters the local dynamic characteristics of the system. As a result, the mechanical impedance is modified by structural damage. Assuming that the properties of the PZT patch remain constant, it turns out that $Z_s(\omega)$ is the structure's impedance that uniquely determines the overall admittance of the electromechanical system. By monitoring the measured EMI and comparing it to a baseline measurement that corresponds to the pristine condition, one can qualitatively determine if incipient structural damage has occurred.

Figure 2:
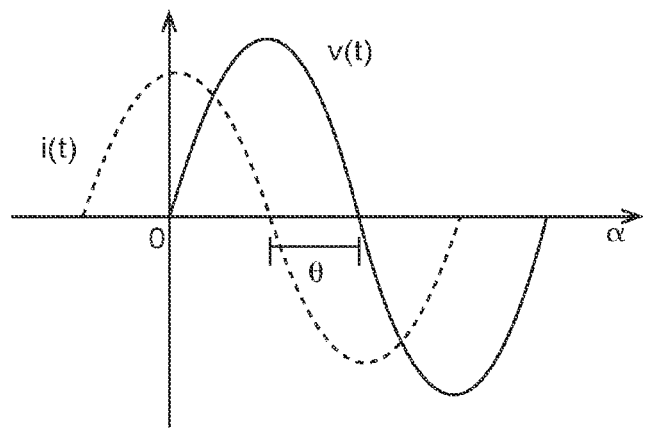
FIG. 2 illustrates example phase displacement between the excitation sine wave v(t), applied to the transducer, and its correspondent circulating current i(t).

The innovative method proposed herein from measuring each EMI FRF is based on the calculation of the resistive part of the electromechanical impedance of the active transducer, at each frequency point of interest, based on a simple and reduced set of equations. FIG. 2 illustrates that the sinusoidal excitation voltage v(t) applied to the transducer creates a similar waveform current i(t) but with a phase shift θ. Equations 2 and 3 mathematically describe these two quantities, where ω is the excitation frequency in [rd/s] and V and I are the amplitude values of the excitation voltage and the circulating current, respectively.

$$v(t) = V\sin(\omega t) \quad (2)$$

$$i(t) = I\sin(\omega t + \theta) \quad (3)$$

The instantaneous power consumed by the transducer, s(t), is obtained by multiplying Equation 2 by Equation 3. Equation 4 presents this result:

$$s(t) = \frac{VI\cos(\theta)}{2} - \frac{VI\cos(2\omega t)\cos(\theta)}{2} + \frac{VI\sin(2\omega t)\sin(\theta)}{2} \quad (4)$$

Figure 3:
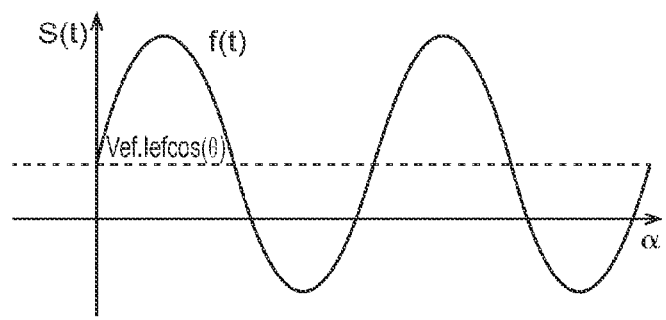
FIG. 3 shows example instantaneous power, s(t), consumed by the transducer (the dashed line illustrates the average consumed power).

The first term of Equation 4 is invariant over the time and includes sufficient information about the phase displacement between v(t) and i(t). FIG. 3 illustrates this term and it is commonly called average power. Equation 5 mathematically defines the average power as a function of the phase displacement between v(t) and i(t):

$$P(\theta) = \frac{VI\cos(\theta)}{2} = V_{RMS} * I_{RMS} * \cos(\theta) \quad (5)$$

Figure 4:
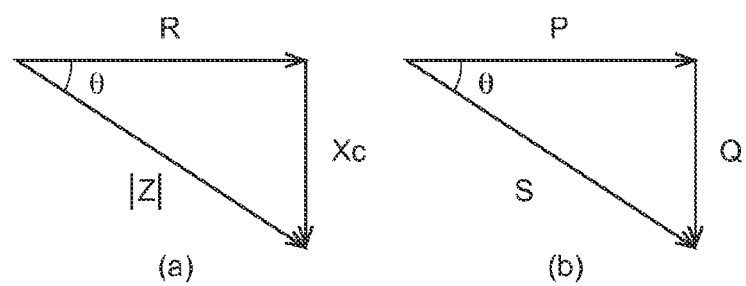
FIGS. 4(a) and 4(b) illustrate example relationships between the components of the electrical impedance (4(a)), and the components of the consumed electrical power of the transducer (4(b)).

The most commonly accepted electrical model of the complex impedance Z of the piezoelectric transducer is illustrated in FIG. 4(a) where R represents the resistive (real) part of the impedance and $X_c$ the reactive (imaginary) part. FIG. 4(b) illustrates the relations between the phase displacement θ, the average power P, the reactive power Q and the apparent power S. Using Equation 5, Ohm's Law and the relations illustrated in FIG. 4, the resistance R can be determined by using Equation 6:

$$R = \frac{P(\theta)}{I_{RMS}^2} \quad (6)$$

Even though the average power is directly dependent on θ, there is no need to directly measure it.

Figure 5:
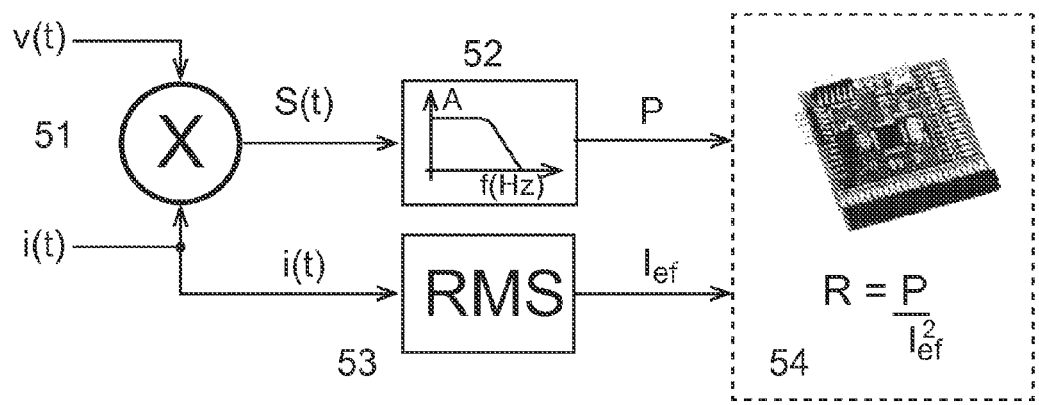
FIG. 5 is a schematic diagram illustrating an example of how the resistive part of the electromechanical impedance can be measured and calculated.

An example non-limiting specialized example circuit, illustrated in FIG. 5, is able to directly measure P(θ). A precision high speed analog multiplier 51 used to obtain s(t). Low pass filter 52 provides a precision gain regulation. RMS-to-DC converter 53 is used to obtain the RMS value of the circulating current in the transducer in the form of a constant voltage value (DC). Microcontroller 54 is used to coordinate the sensing network and to calculate R, by software, using Equation (6). The microcontroller 54 may execute software instructions stored in a non-transitory storage device such as a random access memory, read only memory, flash memory or the like.

The process described is repeated for each frequency point in the previously specified range.

The FIG. 5 circuit acquires the structural health state of an aircraft mechanical component performs measurements at each frequency point of interest by using a network of transducers and working each one simultaneously as actuator and sensor. Each transducer is individually excited by a sinusoidal, constant frequency and arbitrary amplitude, voltage waveform for each arbitrary frequency point used to interrogate the structure. Dedicated hardware executes an analogical (analog) quantization to measure electrical current and average electrical power consumed by each transducer. With these two variables, the electromechanical signature of the structure is obtained at different areas of the monitored structure.

Figure 6:
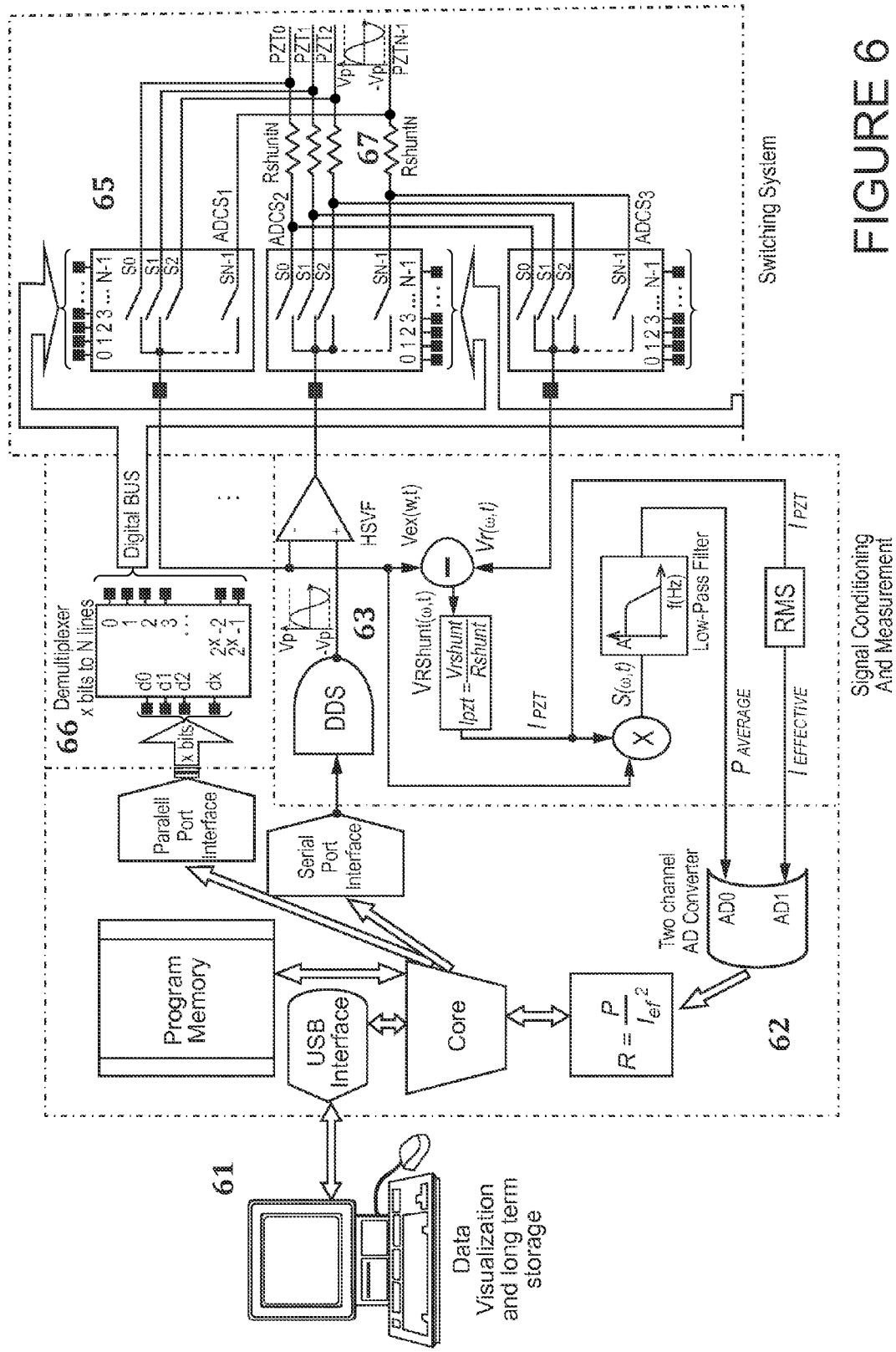
FIG. 6 is a schematic block diagram of an example non-limiting specialized data acquisition system used to measure the EMI FRF of each transducer in the monitoring network.

A more complete block diagram is presented in FIG. 6 where elements proposed in the example non-limiting embodiment are characterized by their functionalities and structures. Computer system 61 implements the man-machine-interface (MMI). Several different interface communications may be implemented to communicate with microcontroller 61. The two analog to digital (AD) channels 62 do not require high sample rates, since $P_{average}$ and $I_{effective}$ are DC values. A sample rate of a few kSamples/s is more than enough. A programmable Digital Data Synthesis (DDS) 63 is used to generate a precise, frequency and amplitude, sine wave. Digitally controlled solid state analog switches 64 are highly reliable; these switches individually activate/deactivate each transducer in the sensing network under the control of demultiplexer (decoder) 66 and the microcontroller 61. Shunt resistors 67 are used to sample de circulating current at each transducer.

Figure 7:
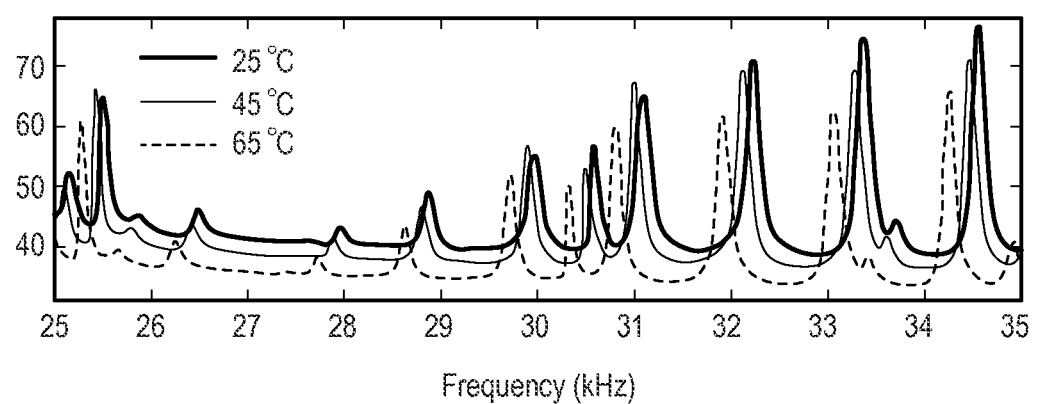
FIG. 7 illustrates example environmental effects of temperature causing frequency and/or amplitude shifts in the EMI FRF.

Environmental effects, such as the temperature illustrated in FIG. 7, can cause frequency and/or amplitude shifts in the EMI FRF. The post-processing algorithms identify and compensate these shifts for a known range of temperature and pressure changes.

Figure 8:
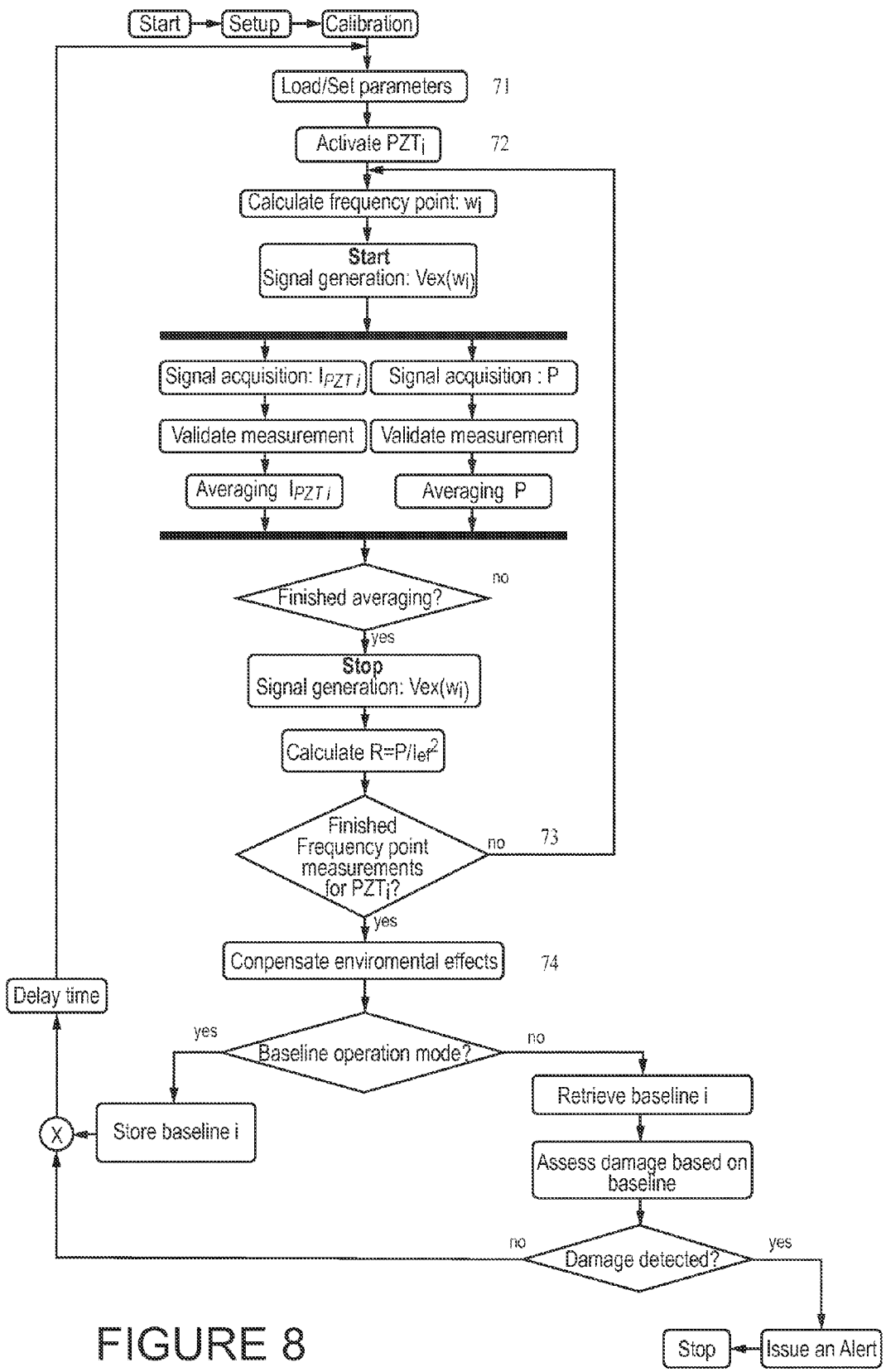
FIG. 8 is a flow chart describing an example non-limiting process implemented to measure each EMI FRF and assess possible damages.

A complete example non-limiting flowchart for damage assessment is illustrated in FIG. 8. Up to step 71, the MMI loads/sets the parameter for the current measurement and further calibrations may also be performed. From 72 to 73, all the processing takes place inside the microcontroller in one example embodiment. From 74 forward, the post processing actions and damage assessments take place inside the computer system in this example embodiment.

After start, setup and calibration, the system loads/sets parameters (71) and activates the PZT transducers. The system calculates a frequency point and then starts signal generation. Two kinds of signal acquisition (current and power are acquired and respectively averaged. R is then calculated straightforwardly from I and P. This process can be repeated for multiple frequency points. Once the process has been performed for each of plural frequency points as desired, the system compensates for environmental effects. Then, if the data acquisition is for baseline purposes, the results are stored. If not baseline, then the results are compared with previously stored baseline information to assess damage based on the baseline. If damage is detected, an alert can be issued automatically to a pilot, crew or maintenance person.

The technology herein may be embodied as a method, system hardware, embedded firmware and or software as a whole product or as a set of parts that work together in order to achieve the same or similar goal.

The software part can be organized into two main sets. The first, called firmware, may be embedded in a microcontroller or any other processing system where preprocessing algorithms (averaging, analog and digital quantization and communication interfaces) are implemented to validate, correct and transfer the measurements to a computer system. The second set, called analysis software, can operate on a single or multiple computer (stand-alone) or other processing system either alone or connected in a network where remote operation and data visualization is possible. Post-processing algorithms (environmental effects compensation) and damage assessment can be combined to identify structural modifications (damages) at early stages.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

The invention claimed is:

1. A method for acquiring a health state of an object or a structural component using an EMI technique by performing measurements at each of plural frequency points of an interest bandwidth by using one or more piezoelectric transducers operating as sensors/actuators at the same time, the method comprising:
   a. providing sine wave excitation, at both constant frequency and amplitude, for each of said plural frequency points of the interest bandwidth;
   b. analog quantizing the RMS circulating current and the average consumed power of a said piezoelectric transducer in order to directly measure a resistive part of electromechanical impedance of the object or structural component;

c. compensating for environmental effects; and
d. compensating for static and dynamic loading;
e. wherein the method uses only said one piezoelectric transducer to monitor the health state of a pre-determined area of the object or structure component.

2. The method of claim 1 including using a specialized circuit to perform the analog quantizing of both the average consumed power and the RMS circulating current of the transducer.

3. The method of claim 1 further including using a set of post-processing algorithms to compensate for effects of changes in temperature and pressure applied on the monitored structure or object.

4. The method of claim 1 further including monitoring the health state of metallic or non-metallic objects or structures.

5. The method of claim 1 including not using FFT algorithms to generate EMI FRF responses.

6. The method of claim 1 wherein a sample rate of AD channels requires only a few kSamples/s of sample rate, independently of the excitation frequency applied to the transducer.

7. The method of claim 1 wherein interrogation frequency ranges from 20 kHz to 400 kHz.

8. The method of claim 1 further including using the transducer as both an exciter and a sensor.

9. The system of claim 1 wherein the transducer comprises both the exciter and a sensor.

10. A system that can control a network of transducers in order to monitor structures, comprising:
an exciter structured to excite a mechanical object or structure with sine wave excitation for each frequency point of interest;
a single transducer coupled to the mechanical object or structure used to monitor the health state of a pre-determined area of the object or structure;
an analog quantizer that quantizes an RMS circulating current and an average consumed power of the transducer in order to directly measure a resistive part of the electromechanical impedance; and
a processor coupled to the analog quantizer that compensates for environmental effects and static and dynamic loading.

11. The system of claim 10 wherein the exciter excites at both constant frequency and amplitude.

12. The system of claim 10 wherein the single transducer and the exciter comprise the same component.

13. The system of claim 10 wherein the processor is operative to manage a multiplexing/demultiplexing of the network and performs included electromechanical impedance calculations.

14. The system of claim 10 wherein the system is a portable system that is battery powered.

15. The system of claim 10 wherein the analog quantizer comprises a specialized circuit to quantize both the average consumed power and the RMS circulating current of the transducer.

16. The system of claim 10 wherein the processor is configured to use a set of post-processing algorithms to compensate for effects of changes in temperature and pressure applied on the monitored object or structure.

17. The system of claim 10 wherein the mechanical object or structure comprises metal or non-metal.

18. The system of claim 10 wherein the processor is configured to not use FFT algorithms to generate EMI FRF responses.

19. The system of claim 10 wherein the analog quantizer is configured to use a sample rate of AD channels requiring only a few kSamples/s of sample rate, independently of the excitation frequency applied to the exciter.

20. The system of claim 10 wherein an interrogation frequency of the exciter ranges from 20 kHz to 400 kHz.

* * * * *